United States Patent
Doyle et al.

(10) Patent No.: US 11,220,688 B2
(45) Date of Patent: *Jan. 11, 2022

(54) OVERSUBSCRIPTION SCHEDULING

(71) Applicant: D2iQ, Inc., San Francisco, CA (US)

(72) Inventors: Connor Patric Doyle, San Francisco, CA (US); Christoforos Kozyrakis, San Francisco, CA (US); Niklas Quarfot Nielsen, San Francisco, CA (US)

(73) Assignee: D2iQ, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/900,750

(22) Filed: Jun. 12, 2020

(65) Prior Publication Data

US 2020/0385726 A1 Dec. 10, 2020

Related U.S. Application Data

(63) Continuation of application No. 15/227,348, filed on Aug. 3, 2016, now Pat. No. 10,733,023.

(Continued)

(51) Int. Cl.
*G06F 9/48* (2006.01)
*G06F 9/50* (2006.01)
(Continued)

(52) U.S. Cl.
CPC ........ *C12N 15/113* (2013.01); *A61K 49/0054* (2013.01); *C12N 15/1135* (2013.01); *C12Q 1/6886* (2013.01); *G06F 9/4881* (2013.01); *G06F 9/5038* (2013.01); *C08G 2261/1432* (2013.01); *C08G 2261/18* (2013.01); *C08G 2261/228* (2013.01); *C08G 2261/3324* (2013.01); *C08G 2261/78* (2013.01); *C12N 2310/11* (2013.01); *C12N 2310/351* (2013.01); *C12N 2310/3515* (2013.01); *C12N 2310/51* (2013.01); *C12N 2320/11* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 7,343,363 B1 * | 3/2008 | Parker | G06N 5/02 706/45 |
| 8,706,798 B1 * | 4/2014 | Suchter | H04L 43/0876 709/202 |

(Continued)

OTHER PUBLICATIONS

Lo et al. "Heracles: improving resource efficiency at scale." ACM SIGARCH Computer Architecture News. vol. 43. No 3. ACM, 2015.

*Primary Examiner* — Lewis A Bullock, Jr.
*Assistant Examiner* — Gilles R Kepnang
(74) *Attorney, Agent, or Firm* — Van Pelt, Yi & James LLP

(57) ABSTRACT

A system for adjusting oversubscription loading includes an interface and a processor. The interface is configured to receive a set of performance data from a set of worker systems. The processor is configured to determine a feedback indication for a worker system of the set of worker systems based at least in part on the set of performance data. The feedback indication is used to adjust an oversubscription controller on the worker system. The processor is configured to provide the feedback indication to the worker system.

15 Claims, 7 Drawing Sheets

Related U.S. Application Data

(60) Provisional application No. 62/202,042, filed on Aug. 6, 2015.

(51) Int. Cl.
*C12N 15/113* (2010.01)
*A61K 49/00* (2006.01)
*C12Q 1/6886* (2018.01)

(52) U.S. Cl.
CPC ........ *C12N 2320/32* (2013.01); *G06F 9/4887* (2013.01); *G06F 9/5027* (2013.01); *G06F 9/5083* (2013.01); *G06F 2209/501* (2013.01)

(56) References Cited

U.S. PATENT DOCUMENTS

| | | |
|---|---|---|
| 8,826,284 B1 | 9/2014 | Fuller |
| 9,535,765 B1 | 1/2017 | Konerding |
| 2003/0237084 A1 | 12/2003 | Neiman |
| 2006/0161920 A1 | 7/2006 | An |
| 2007/0011683 A1 | 1/2007 | Helander |
| 2011/0154350 A1 | 6/2011 | Doyle |
| 2012/0096468 A1 | 4/2012 | Chakravorty |
| 2012/0110550 A1* | 5/2012 | Ghosh ................. G06F 9/44589 717/126 |
| 2012/0110580 A1 | 5/2012 | Ghosh |
| 2013/0312006 A1 | 11/2013 | Hardman |
| 2014/0033223 A1 | 1/2014 | Swart |
| 2014/0122546 A1 | 5/2014 | Liao |
| 2014/0181833 A1 | 6/2014 | Bird |
| 2014/0379619 A1 | 12/2014 | Permeh |
| 2015/0113539 A1 | 4/2015 | Agarwal |
| 2015/0205634 A1 | 7/2015 | McPherson |
| 2015/0363113 A1* | 12/2015 | Rahman ................ G06F 3/0673 707/718 |
| 2016/0062929 A1* | 3/2016 | Yeh ...................... G06F 13/364 710/110 |
| 2016/0103702 A1 | 4/2016 | Schneider |
| 2016/0140001 A1* | 5/2016 | Kulkarni ............... G06F 9/5066 714/4.12 |
| 2016/0246647 A1 | 8/2016 | Harris |
| 2017/0017521 A1* | 1/2017 | Gupta .................. G06F 9/4881 |
| 2017/0026441 A1* | 1/2017 | Moudy ................ G06F 9/5027 |

\* cited by examiner

OVERSUBSCRIPTION SCHEDULING

CROSS REFERENCE TO OTHER APPLICATIONS

This application is a continuation of co-pending U.S. patent application Ser. No. 15/227,348, entitled OVERSUBSCRIPTION SCHEDULING filed Aug. 3, 2016, which claims priority to U.S. Provisional Patent Application No. 62/202,042, entitled FILTER PIPELINES AND BUS ARCHITECTURE FOR OVERSUBSCRIPTION filed Aug. 6, 2015, both of which are incorporated herein by reference for all purposes.

BACKGROUND OF THE INVENTION

High priority services running on a computer cluster underutilize their computing resources in order to maintain enough reserve resources to handle demand spikes of those services without losing performance. However, underutilizing computing resources is inefficient for the computer cluster and wastes computing resources when demand spikes do not appear. To take advantage of the underutilization, low priority services are allowed to operate that are evicted when high priority services need more computing resources. The oversubscription creates the potential that services will be competing for the same limited resource (e.g., central processing unit capacity, free memory, network bandwidth, etc.) in the event that two services have a demand spike.

BRIEF DESCRIPTION OF THE DRAWINGS

Various embodiments of the invention are disclosed in the following detailed description and the accompanying drawings.

DETAILED DESCRIPTION

Figure 1:
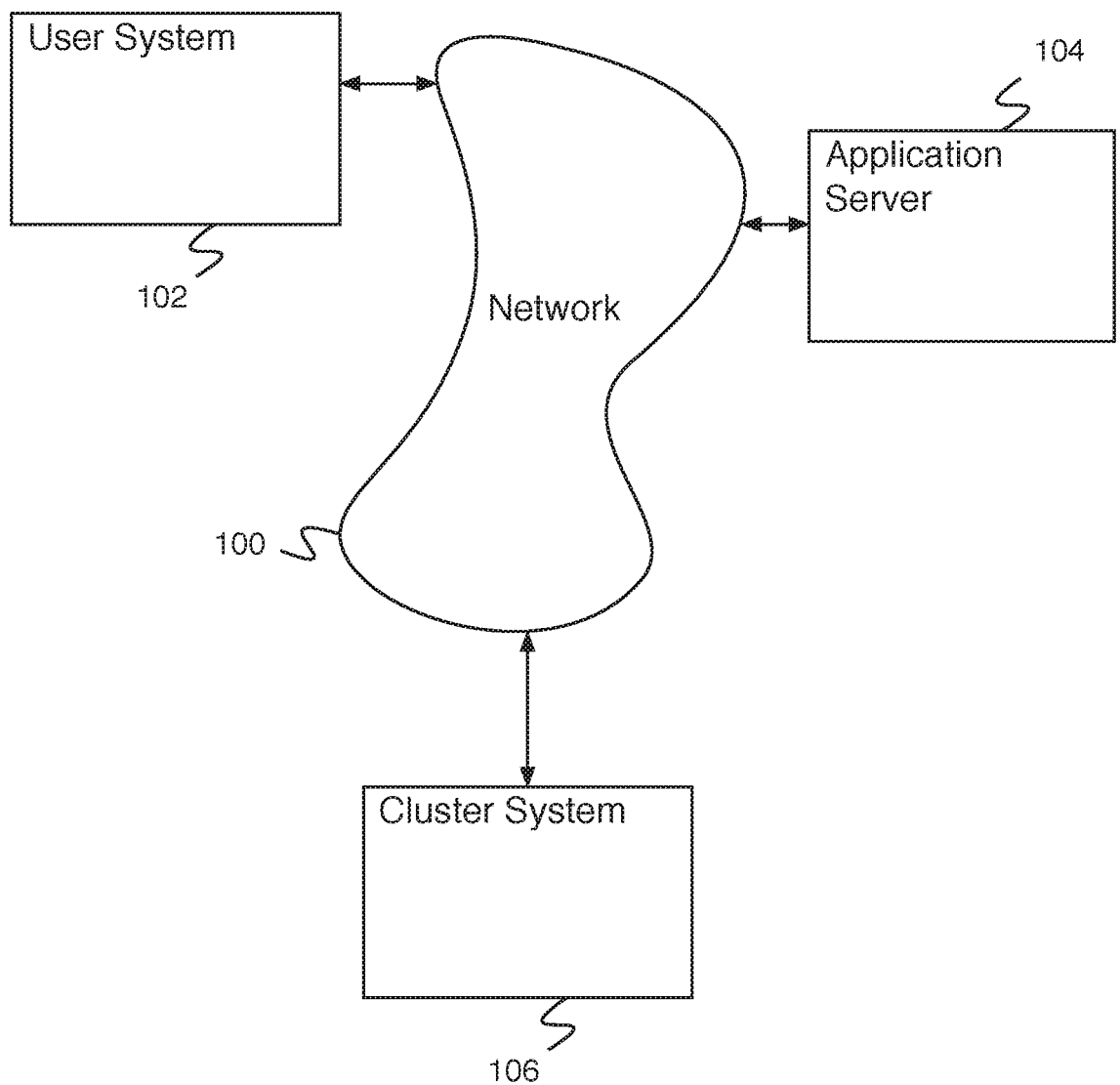
FIG. 1 is a block diagram illustrating an embodiment of a network system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for adjusting oversubscription loading comprises an interface to receive a set of performance data from a set of worker systems, and a processor to determine a feedback indication for a worker system of the set of worker systems based at least in part on the set of performance data, wherein the feedback indication is used to adjust an oversubscription controller on the worker system, and provide the feedback indication to the worker system. The system for adjusting oversubscription loading comprises a memory coupled to the processor and configured to provide the processor with instructions.

In some embodiments, a cluster computing system comprises a master system and a set of worker systems. The master system assigns jobs to the worker systems and compiles job results from the worker systems. Some jobs assigned by the master system comprise high-priority jobs (e.g., jobs where latency is very important, user-facing jobs, etc.). Some jobs assigned by the master system comprise low-priority jobs (e.g., background maintenance tasks, non-critical path tasks, etc.). The master system assigns high-priority jobs to each worker system up to a subscription threshold. The master system additionally attempts to oversubscribe the worker systems by assigning low-priority jobs to increase system utilization past the subscription threshold. Each worker system comprises a local oversubscription controller providing a feedback control to evict low-priority jobs in the event computing resources are required by a high-priority job. In addition, the master system comprises a global feedback controller providing a feedback control to the worker systems. Each worker system provides performance data to the master system and receives a feedback indication used to adjust its local oversubscription controller. The global feedback controller comprises a set of decision-making processes for guiding the feedback indications. In various embodiments, the decision-making processes comprise a stability indicator based decision-making process, a software experiment based decision-making process, a task interference based decision-making process, a performance data classification based decision-making process, or any other appropriate decision-making process.

In some embodiments, the global feedback controller learns from events that occur on each worker system and applies the knowledge to all worker systems. For instance, a task interference based decision-making process on the global feedback controller watches for incidents of tasks interfering on a worker system and ensures that those tasks do not conflict on any worker system. As an example, it may be found that a process for maintaining synchronization of a database with a database on a remote server, normally considered to be a low-priority background process, randomly makes large network communication requests. If the database synchronization process is assigned to a worker system that is also responsible for a low-latency customer communication process, the network requirements of the synchronization process can randomly cause the communication process to not be able to meet its quality of service requirements. If this conflict is observed occurring on a worker system, the global feedback controller can learn to avoid assigning or to never assign those two processes to the same worker system again, avoiding that same conflict from occurring on any other worker system.

FIG. 1 is a block diagram illustrating an embodiment of a network system. In some embodiments, the network system of FIG. 1 comprises a system for oversubscription scheduling. In the example shown, FIG. 1 comprises network 100. In various embodiments, network 100 comprises one or more of the following: a local area network, a wide area network, a wired network, a wireless network, the Internet, an intranet, a storage area network, or any other appropriate communication network. User system 102, application server 104, and cluster system 106 communicate via network 100. In some embodiments, user system 102 comprises a computing system client. In various embodiments, user system 102 comprises a client system for requesting computing jobs, for creating computing jobs, for managing a computing cluster, for data analysis programming, or for any other appropriate purpose. In some embodiments, user system 102 comprises a computing system with which a user interacts directly. Cluster system 106 comprises a cluster computing system. In various embodiments, cluster system 106 comprises a cluster computing system for performing computing jobs, for analyzing data, for responding to a user request, or for any other appropriate purpose. In various embodiments, cluster system 106 comprises a cluster for performing high-priority jobs, for performing user-facing jobs, for performing low-latency jobs, or for performing any other appropriate jobs. Application server 104 comprises a server for providing applications. In some embodiments, applications provided by application server 104 are accessed by user system 102. In some embodiments, application server 104 provides jobs to cluster system 106. In some embodiments, user system 102 comprises a processor and a memory. In various embodiments, user system 102 comprises a single-processor computer, a multiple-processor computer, a plurality of computers, a mobile computer, a tablet computer, or any other appropriate computer. In some embodiments, cluster system 106 comprises a processor and a memory. In some embodiments, cluster system 106 comprises a cluster of computers (e.g., a plurality of interconnected computers for executing a large computing job at a set of small pieces). In various embodiments, each of the one or more computers of cluster system 106 comprises a single-processor computer, a multiple-processor computer, a plurality of computers, a mobile computer, a tablet computer, or any other appropriate computer. In some embodiments, application server 104 comprises a processor and a memory. In various embodiments, application server 104 comprises a single-processor computer, a multiple-processor computer, a plurality of computers, a mobile computer, a tablet computer, or any other appropriate computer.

Figure 2:
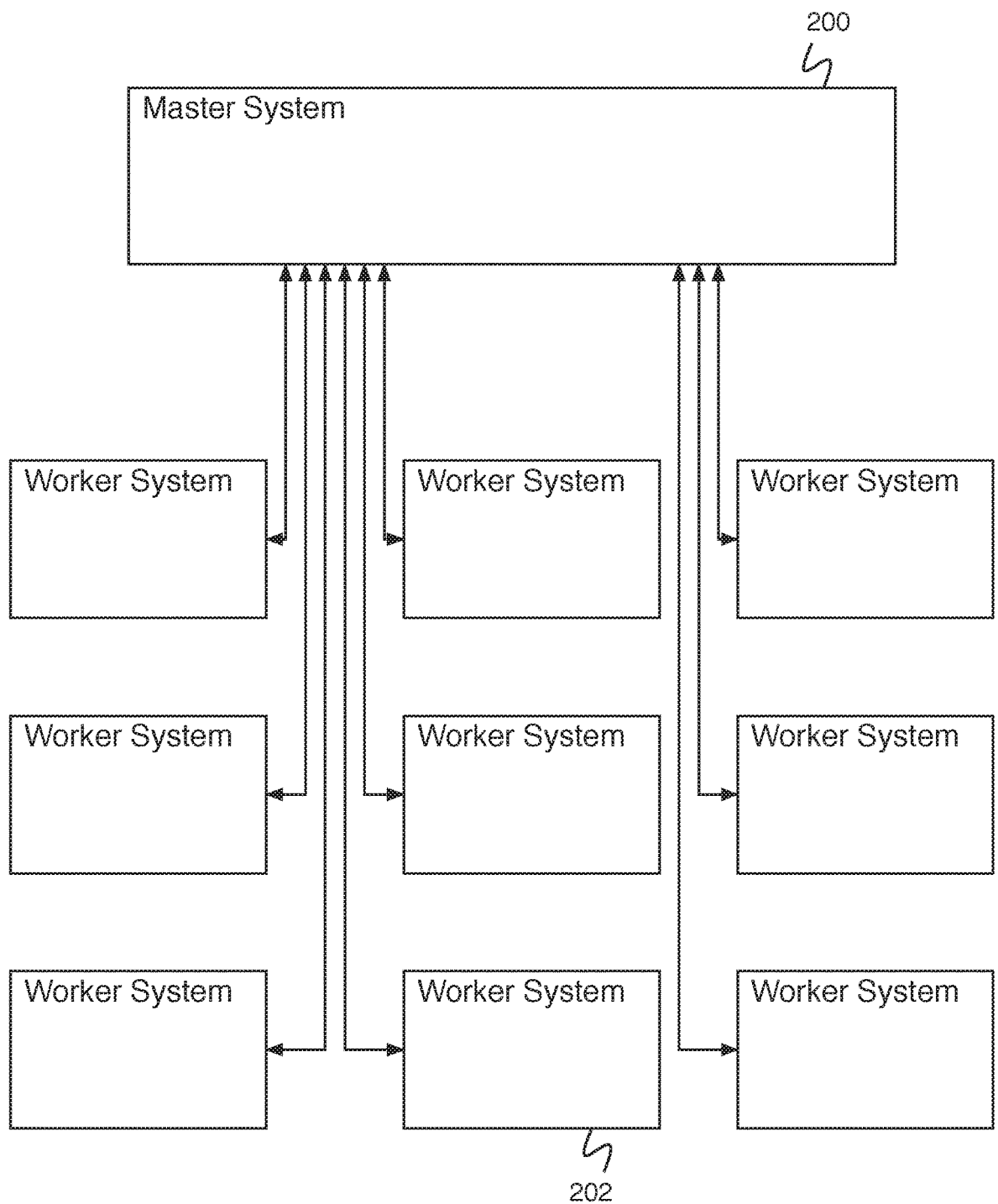
FIG. 2 is a block diagram illustrating an embodiment of a cluster system.

FIG. 2 is a block diagram illustrating an embodiment of a cluster system. In some embodiments, the cluster system of FIG. 2 implements cluster system 106 of FIG. 1. In the example shown, the cluster system of FIG. 2 comprises master system 200. The cluster system of FIG. 2 additionally comprises a plurality of worker systems (e.g., worker system 202). In the example shown, the cluster system of FIG. 2 comprises 9 worker systems. In various embodiments, the cluster system of FIG. 2 comprises 2, 4, 8, 9, 13, 16, 19, 32, 48, 64, 123, 128, 256, 1024, 2048, 4096, 10287, or any other appropriate number of worker systems. In some embodiments, worker systems comprise worker systems for performing jobs. In some embodiments, jobs comprise high-priority jobs or low-priority jobs. In some embodiments, the worker systems each comprise an oversubscription controller creating a feedback loop for controlling oversubscription (e.g., for ensuring that low-priority jobs do not prevent high-priority jobs from accessing the resources they need). In some embodiments, an oversubscription controller provides performance data to master system 200. Master system 200 aggregates performance data from one or more or all worker systems and performs analysis to determine positive and negative performance of the oversubscription controllers on the worker systems to determine improvements for the oversubscription controllers. In some embodiments, an oversubscription controller receives a feedback indication from master system 200 that is used to adjust the feedback loop on the worker system. In various embodiments, master system 200 comprises a master system for receiving job requests from a job requestor, for dividing a job into job segments for completion by worker systems, for providing job segments to worker systems, for receiving job segment results from worker systems, for combining job segment results into job results, for providing job results to a job requestor, for receiving performance data from set of worker systems, for determining a feedback response for each worker system, for providing the feedback response to each worker system, or for any other appropriate purpose.

Figure 3:
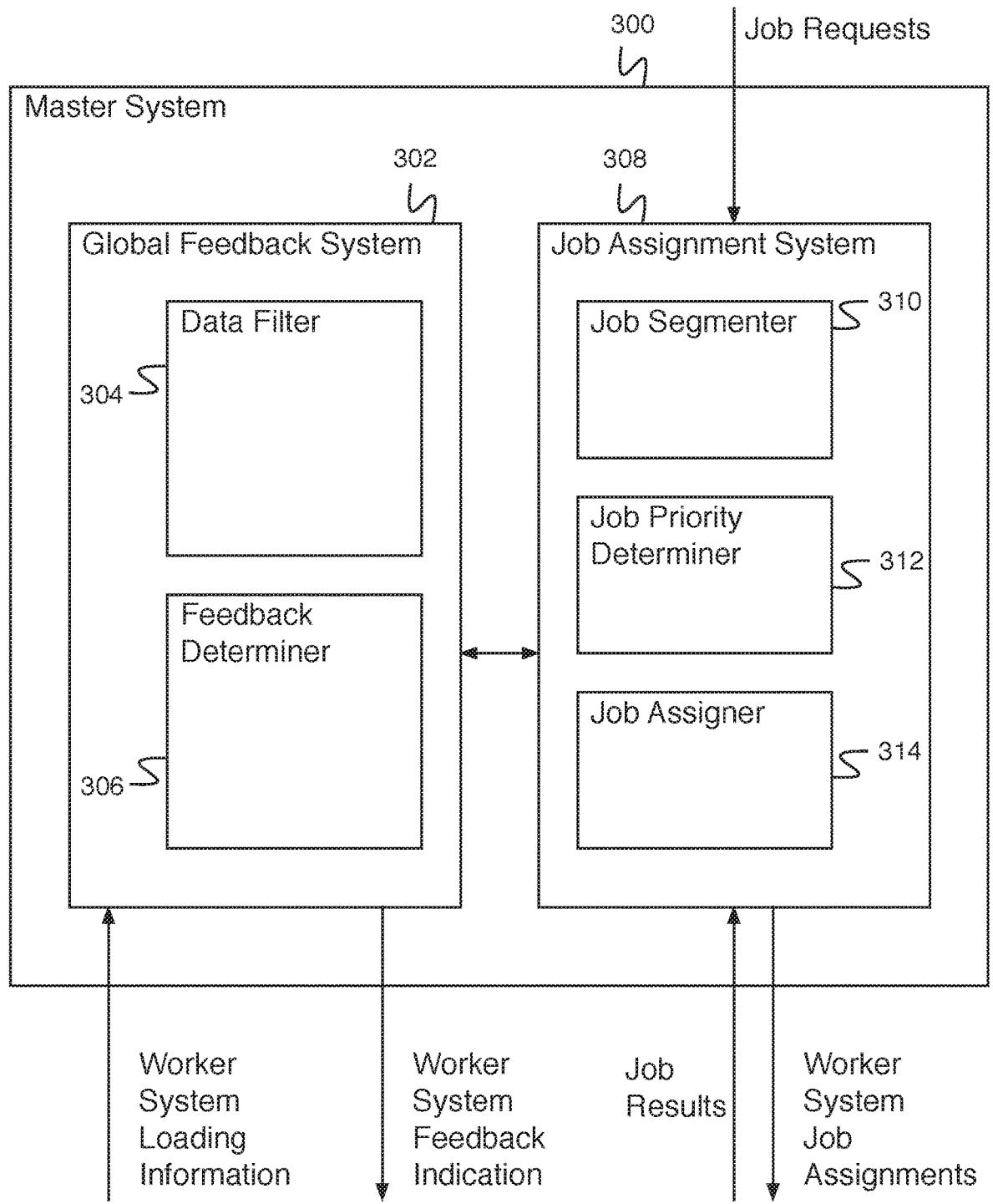
FIG. 3 is a block diagram illustrating an embodiment of a master system.

FIG. 3 is a block diagram illustrating an embodiment of a master system. In some embodiments, master system 300 implements master system 200 of FIG. 2. In the example shown, master system 300 comprises job assignment system 308 and global feedback system 302. In some embodiments, job assignment system 308 comprises a job assignment system for assigning jobs or job segments to worker systems. Job assignment system 308 comprises job segmenter 310. In some embodiments, job segmenter 310 comprises a job segmenter for segmenting a job into a set of job segments. In some embodiments, the set of job segments comprises a set of job segments that can be executed in parallel. In some embodiments the set of job segments comprises a set of job segments that are all the same (e.g., the same job segment is executed multiple times on different data or for any other appropriate reason). In some embodiments, the set of job segments comprises different job segments (e.g., the job comprises a plurality of different tasks). Job assignment system 308 additionally comprises job priority determiner 312. In some embodiments, job priority determiner 312 comprises a priority determiner for determining the priority associated with a job. In some embodiments, job priority determiner 312 determines whether a job priority is a low priority or a high priority. In various embodiments, the job priority is determined on a scale of 1 to 2 (e.g., low or high), on a scale of 1 to 10, on a scale of 1 to 100, or on any other appropriate scale. In some embodiments, job priority determiner 312 determines the priority associated with a job segment (e.g., a job segment segmented by job segmenter 310). In some embodiments, the job priority associated with different segments associated with the same job does not have to be the same priority (e.g., some segments have a low priority and some segments have a high priority). Job assignment system 308 additionally comprises job assigner 314. Job assigner 314 comprises a job assigner for assigning a job to a worker system. In some embodiments, job assigner 314 comprises a job assigner for assigning a job segment to a worker system. In some embodiments, the assignment of a job or a job segment to a worker system is based at least in part on the job priority. In some embodiments, in the event the job comprises a high priority job, job assigner 314 determines a worker system with available high priority capacity and assigns the job to that worker system. In various embodiments, in the event no worker system with available high priority capacity exists in the cluster system, the job is refused, an additional worker system is added, a different high priority job is evicted, or the high priority job overload is addressed in any other appropriate way. In various embodiments, a worker system or each worker system has a subscription threshold limiting the total high priority usage capacity that should be assigned to the system. In various embodiments, the subscription threshold comprises 60% of total capacity, 70% of total capacity, 90% of total capacity, or any other appropriate subscription threshold. In some embodiments, in the event the job comprises a low priority job, job assigner 314 determines an appropriate worker system for the low priority job and assigns the job to that worker system. In various embodiments, an appropriate worker system for the low priority job comprises a worker system with available low priority capacity, a worker system with no conflicting processes running, a worker system running jobs with a different performance data classification than the low priority job, a worker system running jobs experimentally determined to be compatible with the low priority job, or any other appropriate worker system. In various embodiments, worker systems have any number of priority levels associated with executing of a job or job segment where higher priority jobs are less likely to be evicted and lower priority jobs are more likely to be evicted based on different decision criteria for each priority level.

In the example shown in FIG. 3, global feedback system 302 comprises data filter 304 and feedback determiner 306. In some embodiments, global feedback system 302 comprises a global feedback system for receiving worker system loading information from a set of worker systems and providing worker system feedback information to the set of worker systems. Data filter 304 comprises a data filter for filtering data. In various embodiments, filtering data comprises smoothing data, removing noise from data, shaping data, transforming data types, detecting data shifts (e.g., jumps, drops, etc.), throttling estimates, blocking data, etc. In some embodiments, data filter 304 comprises a data filter pipeline (e.g., a set of filters, a feedback configuration of filters, etc.). Feedback determiner 306 comprises a feedback determiner for determining worker system feedback information. In some embodiments, feedback determiner 306 determines feedback information from filtered data from data filter 304. In various embodiments, the feedback information is determined based at least in part on a stability indicator, on a software experiment, on a task interference, on a classification of performance data, or on any other appropriate feedback information determination. In some embodiments, job assignment system 308 communicates with global feedback system 302 as part of the process of assigning jobs. In various embodiments, job assignment system 308 communicates with global feedback system 302 as part of the process of assigning jobs to determine a least loaded system, to determine a least conflicting system, to determine a system with the most available memory, to determine a system with the most available network bandwidth, or to determine any other appropriate system. Master system 300 has one or more processors to execute the functionality of job assignment system 308 and global feedback system 302 as well as one or more memories coupled to the one or more processors that store instructions that are provided to the one or more processors.

Figure 4:
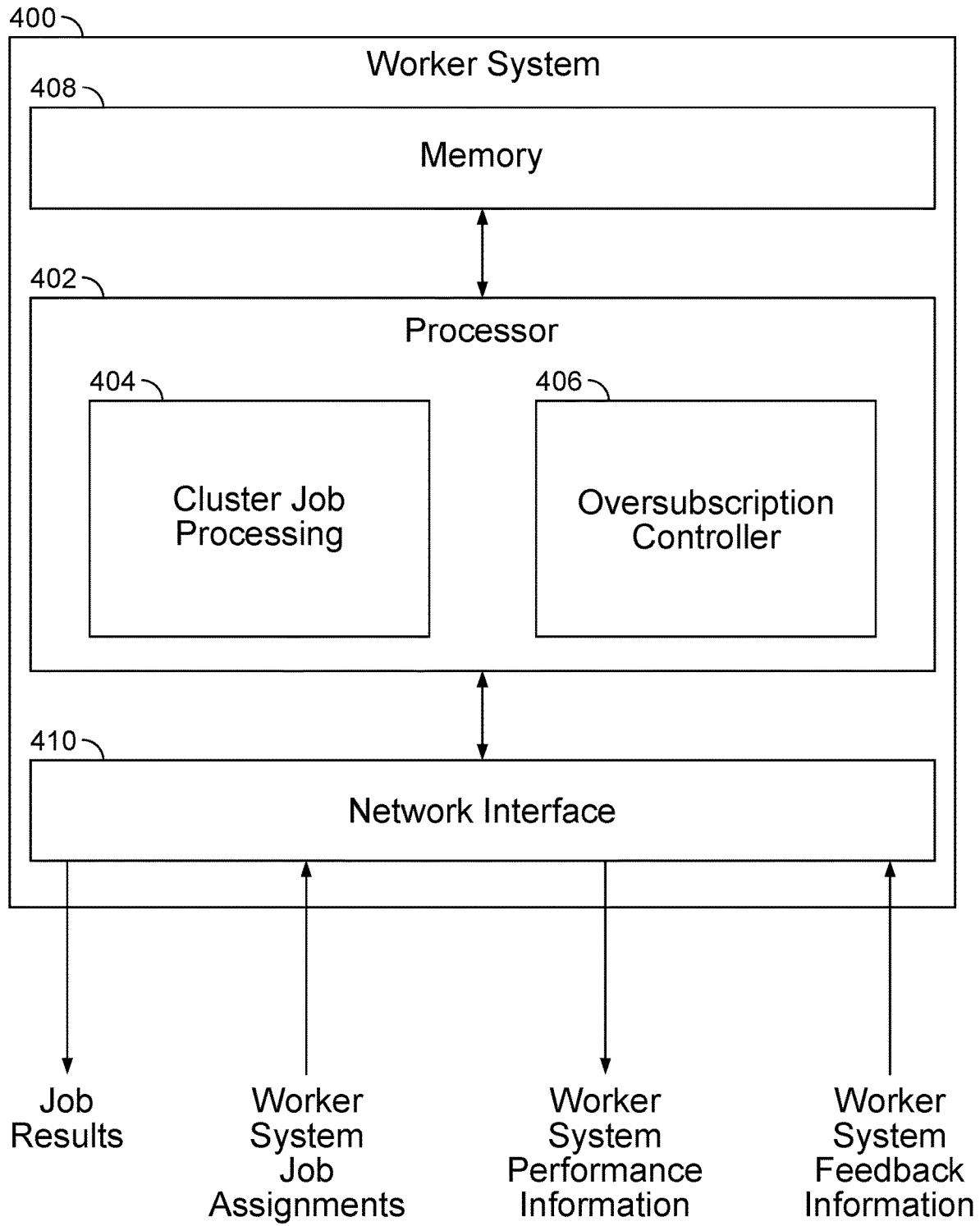
FIG. 4 is a block diagram illustrating an embodiment of a worker system.

FIG. 4 is a block diagram illustrating an embodiment of a worker system. In some embodiments, worker system 400 comprises a worker system of FIG. 2 (e.g., worker system 202). In the example shown, worker system 400 comprises processor 402, memory 408, and network interface 410. In some embodiments, worker system 400 comprises a worker system for processing job assignments. In some embodiments, worker system 400 receives job assignments from a master system (e.g., via network interface 410). In some embodiments, worker system 400 processes job assignments using cluster job processing 404 of processor 402. Cluster job processing 404 comprises processing capacity of processor 402 for processing jobs. In some embodiments, cluster job processing provides job results to a master system (e.g., via network interface 410). Processor 402 additionally comprises oversubscription controller 406. In some embodiments, oversubscription controller 406 comprises an oversubscription controller for controlling loading on cluster job processing 404. In some embodiments, oversubscription controller 406 monitors jobs on cluster job processing 404 (e.g., high priority jobs and low priority jobs). In some embodiments, oversubscription controller 406 evicts jobs on cluster job processing 404 (e.g., remove jobs from processing). In some embodiments, oversubscription controller 406 evicts jobs on cluster job processing 404 based on an eviction criterion. In various embodiments, an eviction criterion comprises newest first, most processor use first, most memory use first, most network use first, or any other appropriate eviction criterion. In some embodiments, oversubscription controller 406 provides worker system loading information to a master system (e.g., via network interface 410). In various embodiments, worker system performance information comprises a number of jobs running, a processor load, a list of jobs running, a memory capacity used, a network interface capacity full, or any other appropriate loading information. In some embodiments, oversubscription controller 406 receives worker system feedback information from a master system (e.g., via network interface 410). In various embodiments, feedback information comprises a loading set point (e.g., a processor loading set point, a memory loading set point, a network interface loading set point), an eviction criteria (e.g., newest first, most processor loading first, most memory loading first, most network loading first, etc.), a job conflict (e.g., a pair of jobs determined to conflict with one another), or any other appropriate feedback information. Memory 408 comprises a memory for storing data. In various embodiments, memory 408 comprises a memory for storing system data, for storing feedback controller data, for storing cluster job data, for storing instructions for the processor, or for storing any other appropriate data or instructions. Network interface 410 comprises a network interface for communicating with a network.

Figure 5:
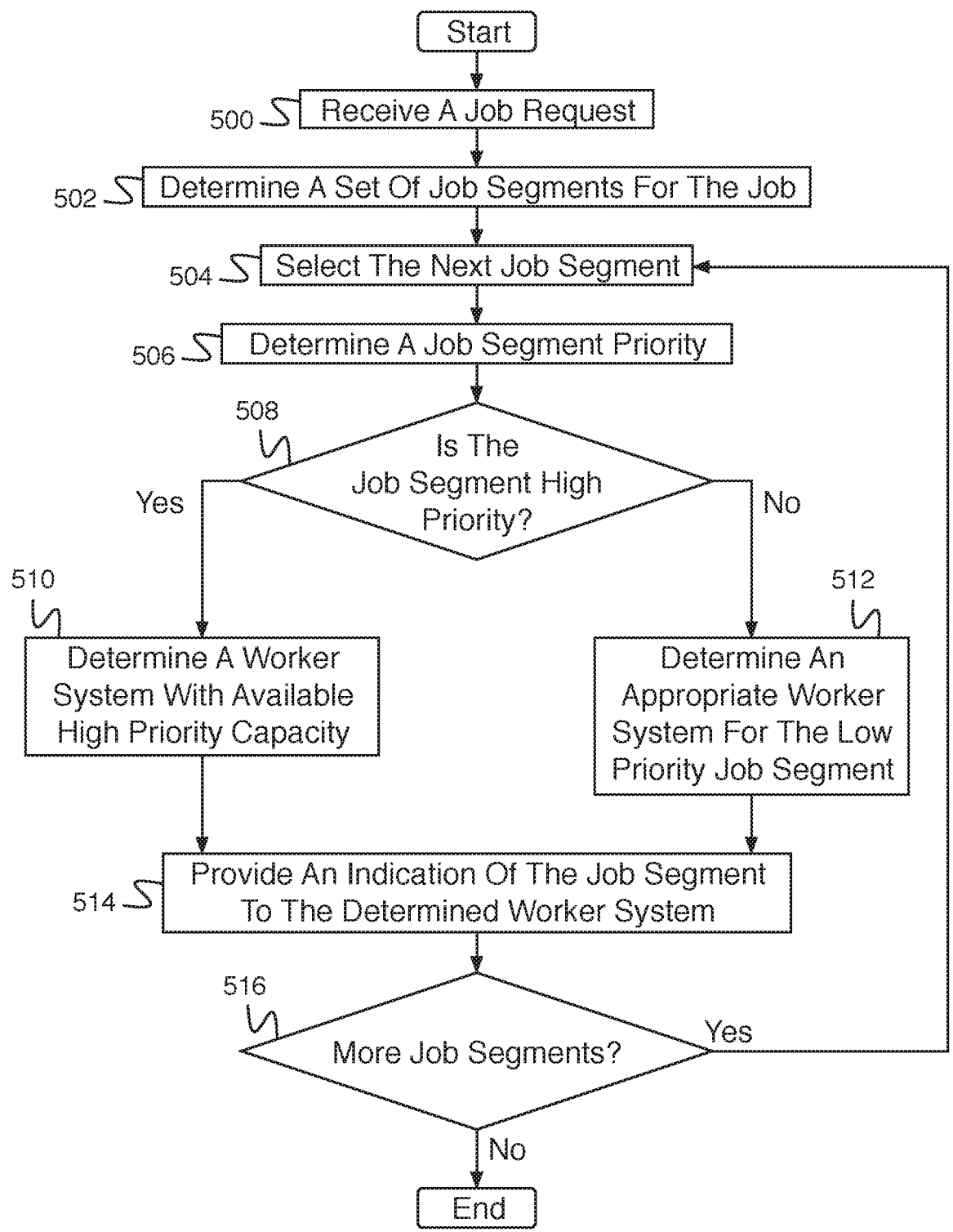
FIG. 5 is a flow diagram illustrating an embodiment of a process for assigning a job.

FIG. 5 is a flow diagram illustrating an embodiment of a process for assigning a job. In some embodiments, the process of FIG. 5 is executed by job assignment system 308 of FIG. 3. In the example shown, in 500, a job request is received. In some embodiments, a job request is received from a user system. In some embodiments, a job request comprises an associated job priority. In 502, a set of job segments for the job is determined. In some embodiments, a set of job segments comprises a set of smaller jobs that can be completed in parallel to complete the job request. In 504, the next job segment is selected. In some embodiments, the next job segment comprises the first job segment. In 506, a job segment priority is determined. In various embodiments, the job segment priority comprises a job segment priority received with a job request, a job segment priority determined based at least in part on a critical path determination, a job segment priority determined based at least in part on a determination of a non-user facing function, or a job segment priority determined in any other appropriate way. In 508, in the event the job segment is not high priority, control passes to 512. In the event the job segment is high priority, control passes to 510. In 510, a worker system with available high priority capacity is determined. In some embodiments, the worker system is determined by querying the worker systems for their available capacity. In some embodiments, the worker system is determined by querying a global feedback system. Control then passes to 514. In 512, an appropriate worker system for the low priority job segment is determined. In various embodiments, an appropriate worker system for the low priority job segment comprises a worker system with available low priority capacity, a worker system running jobs that are compatible with the low priority job segment, a worker system running jobs that utilize different resources than the low priority job segment, or any other appropriate worker system. Control then passes to 514. In 514, an indication of the job segment is provided to the determined worker system. For example, a worker system is provided with a set of instructions and data that are required in order for the job segment to be executed. In some embodiments, an indication is provided to the determined worker system of a location from which job segment information can be fetched. In 516, it is determined whether there are more job segments. In the event it is determined that there are more job segments, control passes to 504. In the event it is determined that there are not more job segments, the process ends.

Figure 6:
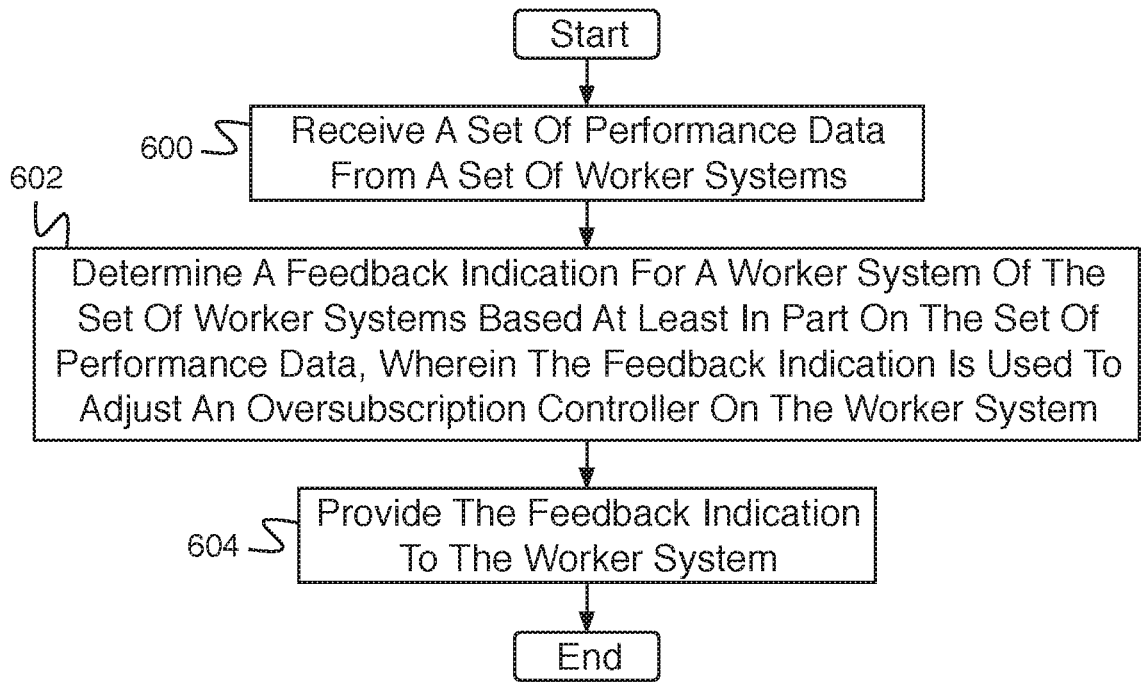
FIG. 6 is a flow diagram illustrating an embodiment of a process for adjusting oversubscription loading.

FIG. 6 is a flow diagram illustrating an embodiment of a process for adjusting oversubscription loading. In some embodiments, the process of FIG. 6 is executed by a global feedback system (e.g., global feedback system 302 of FIG. 3). In the example shown, in 600, a set of performance data is received from a set of worker systems. In 602, a feedback indication for a worker system of the set of worker systems is determined based at least in part on the set of performance data, wherein the feedback indication is used to adjust an oversubscription controller on the worker system. In various embodiments, the feedback indication is based at least in part on a stability indicator, on a software experiment, on a task interference, on a classification of performance data (e.g., processor bound, memory bound, network access bound, etc.), or on any other appropriate feedback determiner. In 604, the feedback indication is provided to the worker system. In various embodiments, the feedback indication causes the oversubscription controller to stop a process, to evict a process, to freeze a process, to halt a process, to throttle a process, to block a process, to not allow a process to execute, to limit access to shared hardware resources by a process, or any other appropriate action.

Figure 7:
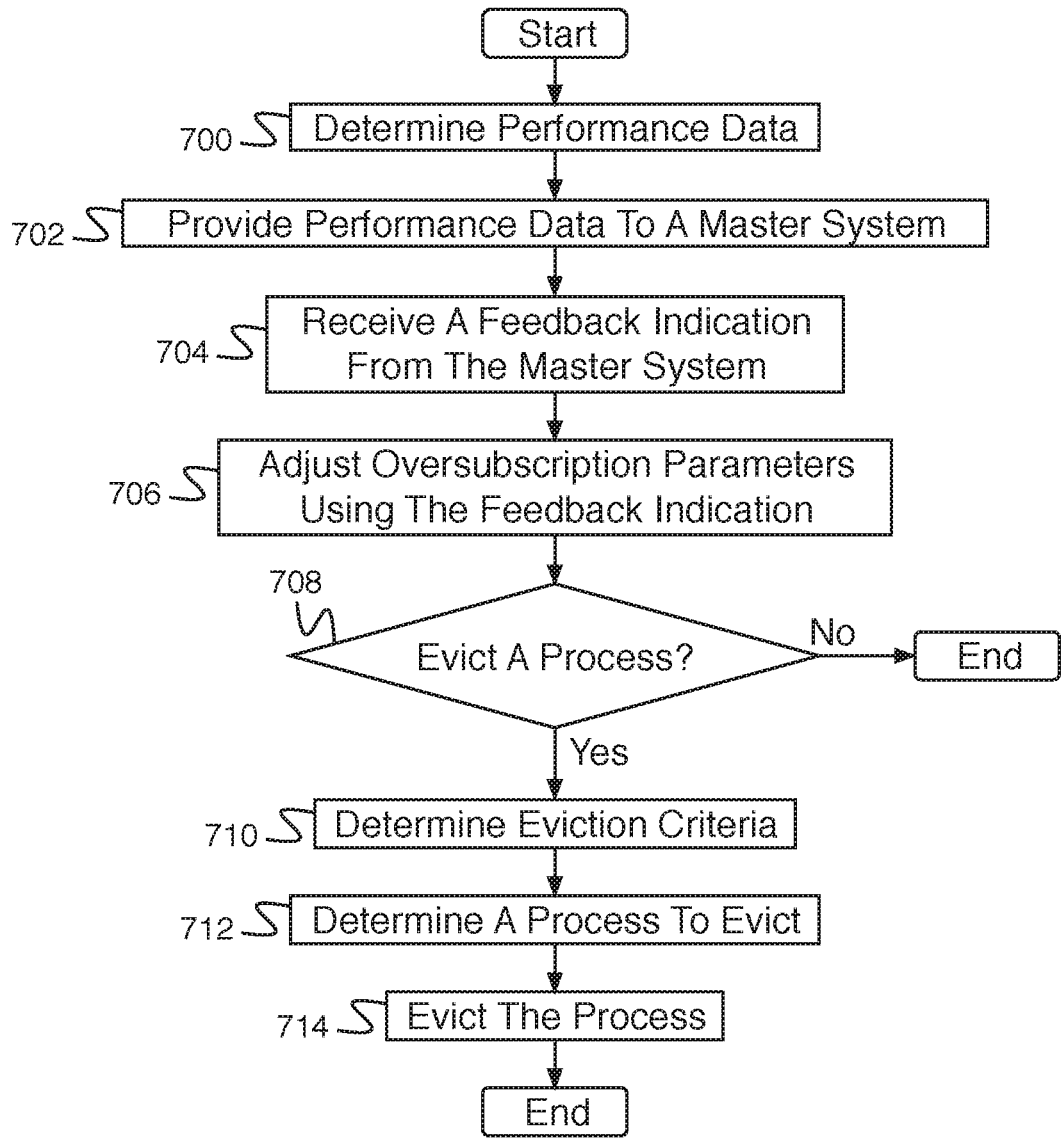
FIG. 7 is a flow diagram illustrating an embodiment of a process for local feedback.

FIG. 7 is a flow diagram illustrating an embodiment of a process for local feedback. In some embodiments, the process of FIG. 7 is executed by oversubscription controller 406 of FIG. 4. In the example shown, in 700, performance data is determined. In various embodiments, determining performance data comprises determining processor loading, determining a list of jobs running, determining memory loading, determining network loading, determine disk loading, or determining any other appropriate performance data. In 702, performance data is provided to a master system. In 704, a feedback indication is received from the master system. In 706, the feedback indication is used to adjust oversubscription parameters. In various embodiments, oversubscription parameters comprise a set point (e.g., a processor loading set point, a memory usage set point, a network usage set point, etc.), an eviction criteria (e.g., newest first, most processor use first, most memory use first, most network use first, etc.), or any other appropriate oversubscription parameters. In 708, it is determined whether to evict a process. In some embodiments, it is determined whether to evict a process using the oversubscription parameters. In the event it is determined not to evict a process, the process ends. In the event it is determined to evict a process, control passes to 710. In 710, eviction criteria are determined. In 712, a process to evict is determined (e.g., according to the eviction criteria). In 714, the process is evicted (e.g., terminated). In some embodiments, the process of FIG. 7 is continuously performed during the execution of job segments by a worker system.

In some embodiments, a performance data comprises a stability indicator data. The stability indicator data is a measurement of how an application is able to perform (or not perform) requests that are sent to it—for example, response time. In some embodiments, a feedback indication is provided in the event that the stability indicator data indicates a number of response time that is higher than a maximum response time threshold (e.g., $95^{th}$ percentile response time increases over a threshold of 100 ms, x percentile over a y threshold value, etc.). The feedback indication provided to an oversubscription controller comprises a throttling indication (e.g., evict the interfering process). In various embodiments, a feedback indication is provided in the event that a data is above a maximum, below a minimum, between two thresholds, outside of two thresholds, or any other appropriate criteria. In various embodiments, the feedback indication causes the oversubscription controller to halt a process, to block a process, to not allow a process to execute, to limit access to shared hardware resources by a process, or any other appropriate action.

In some embodiments, a performance data comprises a software experiment data. The software experiment data compares the performance of a workload (e.g., tasks per second performed) under ideal conditions (e.g., no potentially interfering workloads present on the same worker) with its performance with one or more other workloads present. The outcome is used to determine the placement of oversubscribed tasks. In some embodiments, a feedback indication is provided in the event that the software experiment data indicates the drop in performance that is greater than a maximum drop threshold (e.g., 95th percentile response time increases above a threshold of 100 milliseconds, x percentile over a y threshold value, etc.). The feedback indication provided to an oversubscription controller comprises an interfering workload indication (e.g., evict the interfering process). In various embodiments, a feedback indication is provided in the event that a data is above a maximum, below a minimum, between two thresholds, outside of two thresholds, or any other appropriate criteria. In various embodiments, the feedback indication causes the oversubscription controller to halt a process, to block a process, to not allow a process to execute, to limit access to shared hardware resources by a process, or any other appropriate action.

In some embodiments, a performance data comprises a task interference data. The task interference data is when two tasks that are scheduled on the same worker use shared resources such as the low level CPU cache. If multiple tasks compete for the same cache resources, the cache becomes ineffective. This is called cache pollution and can be used as an indicator of interference. In some embodiments, a feedback indication is provided in the event that the task interference data indicates cache pollution. In some embodiments, a feedback indication is provided in the event that there is memory bandwidth interference. For example, the interfering task consumes much of the available memory bandwidth of the system, which causes performance of other tasks to deteriorate. In various embodiments, a feedback indication is provided in the event that there is cache bandwidth interference, disk IO, network IO, latency attributable to the operating system software (e.g., the process scheduler), or any other appropriate indication. In various embodiments, the feedback indication causes the oversubscription controller to evict a process, to halt a process, to block a process, to not allow a process to execute, to limit access to shared hardware resources by a process, or any other appropriate action.

In some embodiments, a performance data comprises a classification of performance data. The classification of performance data can include a memory intensive application, a processor intensive application, a disk access intensive application, a network access intensive application, or an application with dominant usage of any other system resource.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for adjusting oversubscription loading, comprising:
   an interface configured to:
      receive a set of performance data from a set of worker systems; and
   a processor configured to:
      determine a feedback indication for a worker system of the set of worker systems based at least in part on the set of performance data, wherein the set of performance data includes a stability indicator, a software experiment data, and a task interference, and wherein the feedback indication is used to adjust an oversubscription controller on the worker system, wherein the determining of the feedback indication comprises to:
      perform the following:
         A) determine a response time for an application performing requests sent to the application to obtain the stability indicator; and
            in response to a determination that the response time is greater than or equal to a maximum response time threshold, include the stability indicator in the feedback indicator;
         B) compare tasks over a period of time with no potentially interfering workloads present on a worker with tasks over the period of time with one or more other interfering workloads present on the same worker to obtain the software experiment data; and
            in response to a determination that a decrease in tasks over the period of time is greater than or equal to a maximum decrease threshold, include the software experiment data in the feedback indicator; and
         C) determine whether two or more tasks that are scheduled on the same worker use a shared resource to obtain the task interference; and
            in response to a determination that two or more tasks that are scheduled on the same worker use the shared resource, include the task interference in the feedback indicator;
      provide the feedback indication to the worker system;
      adjust the oversubscription controller based on the provided feedback indication; and
      evict a job based on the adjusted oversubscription controller.

2. The system of claim 1, wherein the classification of performance data comprises a processor intensive classification.

3. The system of claim 1, wherein the classification of performance data comprises a memory intensive classification.

4. The system of claim 1, wherein the classification of performance data comprises a network access intensive classification.

5. The system of claim 1, wherein the feedback indication is used to adjust a set point on the oversubscription controller.

6. The system of claim 5, wherein the set point comprises a desired processor load set point.

7. The system of claim 5, wherein the set point comprises a desired memory usage set point.

8. The system of claim 5, wherein the set point comprises a desired network usage set point.

9. The system of claim 1, wherein the feedback indication is used to adjust an eviction criteria on the oversubscription controller.

10. The system of claim 9, wherein the eviction criteria comprises newest first.

11. The system of claim 9, wherein the eviction criteria comprises most processor use first.

12. The system of claim 9, wherein the eviction criteria comprises most memory use first.

13. The system of claim 9, wherein the eviction criteria comprises most network use first.

14. A method for adjusting oversubscription loading, comprising:
   receiving a set of performance data from a set of worker systems;
   determining, using a processor, a feedback indication for a worker system of the set of worker systems based at least in part on the set of performance data, wherein the set of performance data includes a stability indicator, a software experiment data, and a task interference, and wherein the feedback indication is used to adjust an oversubscription controller on the worker system, wherein the determining of the feedback indication comprises:
   performing the following:
      A) determining a response time for an application performing requests sent to the application to obtain the stability indicator; and
         in response to a determination that the response time is greater than or equal to a maximum response time threshold, including the stability indicator in the feedback indicator;

B) comparing tasks over a period of time with no potentially interfering workloads present on a worker with tasks over the period of time with one or more other interfering workloads present on the same worker to obtain the software experiment data; and in response to a determination that a decrease in tasks over the period of time is greater than or equal to a maximum decrease threshold, including the software experiment data in the feedback indicator; and C) determining whether two or more tasks that are scheduled on the same worker use a shared resource to obtain the task interference; and in response to a determination that two or more tasks that are scheduled on the same worker use the shared resource, including the task interference in the feedback indicator;

providing the feedback indication to the worker system;

adjusting the oversubscription controller based on the provided feedback indication; and evicting a job based on the adjusted oversubscription controller.

15. A computer program product for oversubscription loading, the computer program product being embodied in a non-transitory computer readable storage medium and comprising computer instructions for:

receiving a set of performance data from a set of worker systems;

determining a feedback indication for a worker system of the set of worker systems based at least in part on the set of performance data, wherein the set of performance data includes a stability indicator, a software experiment data, and a task interference, and wherein the feedback indication is used to adjust an oversubscription controller on the worker system, wherein the determining of the feedback indication comprises:

performing the following:

A) determining a response time for an application performing requests sent to the application to obtain the stability indicator; and in response to a determination that the response time is greater than or equal to a maximum response time threshold, including the stability indicator in the feedback indicator;

B) comparing tasks over a period of time with no potentially interfering workloads present on a worker with tasks over the period of time with one or more other interfering workloads present on the same worker to obtain the software experiment data; and in response to a determination that a decrease in tasks over the period of time is greater than or equal to a maximum decrease threshold, including the software experiment data in the feedback indicator; and C) determining whether two or more tasks that are scheduled on the same worker use a shared resource to obtain the task interference; and in response to a determination that two or more tasks that are scheduled on the same worker use the shared resource, including the task interference in the feedback indicator;

providing the feedback indication to the worker system;

adjusting the oversubscription controller based on the provided feedback indication; and evicting a job based on the adjusted oversubscription controller.

\* \* \* \* \*